(12) United States Patent
Mabuchi et al.

(10) Patent No.: US 9,067,178 B2
(45) Date of Patent: *Jun. 30, 2015

(54) BLOOD PURIFIER PACKAGE AND PROCESS FOR MANUFACTURING THE SAME

(75) Inventors: Kimihiro Mabuchi, Otsu (JP); Noriko Monden, Otsu (JP); Noriaki Kato, Otsu (JP); Yuuki Hatakeyama, Osaka (JP); Takashi Sunohara, Osaka (JP); Toshiaki Masuda, Osaka (JP)

(73) Assignee: Nipro Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/721,766

(22) PCT Filed: Dec. 2, 2005

(86) PCT No.: PCT/JP2005/023337
§ 371 (c)(1),
(2), (4) Date: Jan. 25, 2008

(87) PCT Pub. No.: WO2006/068124
PCT Pub. Date: Jun. 29, 2006

(65) Prior Publication Data
US 2008/0142434 A1    Jun. 19, 2008

(30) Foreign Application Priority Data

Dec. 22, 2004    (JP) .............................. P2004-371542

(51) Int. Cl.
*B01D 39/00*    (2006.01)
*B01D 39/14*    (2006.01)
*B01D 67/00*    (2006.01)
*A61L 2/08*    (2006.01)
*A61M 1/16*    (2006.01)

(52) U.S. Cl.
CPC ............ *B01D 67/0097* (2013.01); *A61L 2/087* (2013.01); *A61M 1/16* (2013.01)

(58) Field of Classification Search
USPC ............. 210/500.41, 321.8, 500.23; 426/118; 264/41
See application file for complete search history.

(56) References Cited

U.S. PATENT DOCUMENTS

| | | | |
|---|---|---|---|
| 4,813,210 A | 3/1989 | Masuda et al. | |
| 5,436,068 A | 7/1995 | Kobayashi et al. | |
| 5,441,488 A | 8/1995 | Shimura et al. | |
| 5,641,450 A | 6/1997 | Kobayashi et al. | |
| 5,881,534 A | 3/1999 | Ahlqvist et al. | |
| 5,889,093 A | 3/1999 | Hatakeyama et al. | |
| 6,133,361 A * | 10/2000 | Hatakeyama et al. | 206/524 |
| 6,605,218 B2 * | 8/2003 | Kozawa et al. | 210/500.21 |
| 6,776,912 B2 | 8/2004 | Baurmeister | |
| 7,442,302 B2 | 10/2008 | Mabuchi et al. | |
| 2001/0004976 A1 | 6/2001 | Kozawa et al. | |
| 2002/0051730 A1 * | 5/2002 | Bodnar et al. | 422/33 |
| 2005/0063859 A1 | 3/2005 | Masuda et al. | |
| 2005/0072731 A1 | 4/2005 | Kozawa et al. | |
| 2006/0205309 A1 | 9/2006 | Mabuchi et al. | |
| 2007/0114167 A1 | 5/2007 | Mabuchi et al. | |
| 2007/0187320 A1 | 8/2007 | Mabuchi et al. | |
| 2007/0199891 A1 * | 8/2007 | Mabuchi et al. | 210/500.23 |
| 2008/0000830 A1 | 1/2008 | Mabuchi et al. | |
| 2008/0044643 A1 | 2/2008 | Yokota et al. | |
| 2008/0067122 A1 | 3/2008 | Mabuchi et al. | |
| 2008/0087599 A1 * | 4/2008 | Mabuchi et al. | 210/500.23 |

FOREIGN PATENT DOCUMENTS

| | | |
|---|---|---|
| EP | 0 218 003 A1 | 4/1987 |
| JP | 55-23620 B | 2/1980 |
| JP | 58-134840 A | 8/1983 |
| JP | 62-74364 A | 4/1987 |
| JP | 62-204754 A | 9/1987 |
| JP | 63-111878 A | 5/1988 |
| JP | 4-300636 A | 10/1992 |
| JP | 6-285152 A | 10/1994 |
| JP | 8-168524 A | 7/1996 |

(Continued)

OTHER PUBLICATIONS

Translation of WO98/058842, Hatayama et al., Dec. 1998, WIPO.*
Japanese Patent Office, International Search Report in International Patent Application No. PCT/JP2005/018861 (Jan. 17, 2006).
Japanese Patent Office, International Preliminary Report on Patentability in International Patent Application No. PCT/JP2005/018861 (Apr. 17, 2007).
Japanese Patent Office, Office Action in Japanese Patent Application No. 2004-301771 (Jul. 27, 2010).
Japanese Patent Office, International Search Report in International Patent Application No. PCT/JP2005/018862 (Jan. 24, 2006).
Japanese Patent Office, International Preliminary Report on Patentability in International Patent Application No. PCT/JP2005/018862 (Apr. 17, 2007).

(Continued)

*Primary Examiner* — Dirk Bass
(74) *Attorney, Agent, or Firm* — Leydig, Voit & Mayer, Ltd.

(57) ABSTRACT

Objects of the present invention are to provide a blood purifier package which shows a less increase in the amounts of extracts from the materials of its blood purifier, particularly of its selective permeable separation membranes, attributed to the deterioration of the same materials with time after exposure to a radioactive ray or an electron ray, and which is therefore highly reliable in safety in use for hemocatharsis, and to provide a process for manufacturing the same. The present invention relates to a blood purifier package obtained by packing a blood purifier which comprises selectively permeable separation membranes as a main component, and this blood purifier package is characterized in that the blood purifier is packed and sealed together with an oxygen scavenger in a packaging material capable of shutting out an external air and a water vapor, under a condition of a relative humidity of above 40% RH at 25° C.

1 Claim, No Drawings

(56) References Cited

FOREIGN PATENT DOCUMENTS

| | | |
|---|---|---|
| JP | 10-165773 A | 6/1998 |
| JP | 10-309427 A | 11/1998 |
| JP | 2000-225326 A | 8/2000 |
| JP | 2000-288085 A | 10/2000 |
| JP | 2001-170167 | 6/2001 |
| JP | 2001-205057 A | 7/2001 |
| JP | 2003-245526 A | 9/2003 |
| JP | 2004-195380 A | 7/2004 |
| WO | WO 95/33651 A1 | 12/1995 |
| WO | WO98/58842 * | 12/1998 ............... 210/500.21 |
| WO | WO 98/58842 A1 | 12/1998 |
| WO | 2003/039721 A1 | 5/2003 |

OTHER PUBLICATIONS

European Patent Office, European Search Report in European Patent Application No. EP 045793649 (May 14, 2008).

Japanese Patent Office, International Search Report in International Patent Application No. PCT/JP2005/023337 (Jan. 17, 2006).

Japanese Patent Office, International Preliminary Report on Patentability in International Patent Application No. PCT/JP2005/023337 (Jun. 26, 2007).

European Patent Office, Extended European Search Report in European Application No. 05793644.5 (Sep. 18, 2013).

European Patent Office, Extended European Search Report in European Application No. 05820333.2 (Nov. 19, 2014).

* cited by examiner

BLOOD PURIFIER PACKAGE AND PROCESS FOR MANUFACTURING THE SAME

TECHNICAL FIELD

The present application claims priority based on Japanese Patent Application No. 2004-371542. The contents of that application are incorporated herein by reference thereto in its entirety.

The present invention relates to a blood purifier package and a process for manufacturing the same. In particular, the present invention pertains to a blood purifier package highly reliable in safety in use for hemocatharsis, since the amounts of eluates from its blood purifier, attributed to deterioration of the materials of selectively permeable separation membranes constituting the blood purifier, are smaller. The present invention also relates to a process for manufacturing the same.

BACKGROUND OF THE INVENTION

In hemocatharsis for therapy of renal failure, etc., blood purifiers such as hemodialyzers, hemofilters and hemodiafilters, which comprise dialysing membranes or ultrafilter membranes as separators, are widely used in order to remove urinal toxic substances and waste products in blood. The dialysing membranes and the ultrafilter membranes as separators are made of natural materials such as cellulose or the derivatives thereof (e.g., cellulose diacetate, cellulose triacetate, etc.) or synthetic polymers such as polysulfone, polymethyl methacrylate, polyacrylonitrile, etc. The importance of blood purifiers comprising hollow fiber type selectively permeable separation membranes as separators is very high in the field of dialyzers, in view of the advantages thereof such as the reduction of the amount of extracorporeal circulated blood, high efficiency of removing undesired substances in blood, and high productivity of manufacturing modules.

When the above blood purifier is used as a hemodialyzer, it is necessary to perfectly sterilize the blood purifier before use. For this sterilization, formalin, ethylene oxide gas, high-pressure steam, or exposure to a radioactive ray such as a γ-ray or an electron ray is employed, each of which exhibits its individual effect. Among those, the sterilization by exposure to a radioactive ray or an electronic ray is preferably employed because a subject in a package as it is can be directly subjected to a sterilization treatment, and because the sterilization effect of this method is excellent.

However, it is known that selectively permeable separation membranes for use in such a blood purifier and an adhesive, etc. for use in fixing such membranes tend to deteriorate due to the exposure to a radioactive ray or an electron ray. Under such a circumstance, there are proposed methods for sterilizing blood purifiers while preventing the deterioration of membranes, adhesives, etc. For example, there is disclosed a method of inhibiting the deterioration of hollow fiber membranes due to exposure to γ-ray by maintaining the hollow fiber membranes in a wet state (cf. Patent Literature 1). However, this method has the following problems: the weight of the blood purifier inevitably increases since it is needed to maintain the hollow fiber membranes in a wet state, which leads to disadvantages in transport and handling thereof; or the hollow fiber membranes tend to burst or are damaged under such severely cold conditions that the water used to wet the membranes is frozen. Further, the preparation of a large amount of sterilized water is one of factors for higher cost. Furthermore, there is a possible danger of proliferation of bacteria in a very short time interval between the completion of packaging and the starting of sterilization, since the hollow fiber membranes are intentionally maintained in a wet state which facilitates the proliferation of bacteria. As a result, it takes a long time in completely sterilizing the blood purifier thus manufactured, and undesirably, such a disadvantage induces a higher cost and poor safety.

To avoid the wet state of hollow fiber membranes and to inhibit the deterioration thereof due to exposure to a radioactive ray, a sterilization-protective agent such as glycerin, polyethylene glycol etc. is contained in the hollow fiber membranes, and such hollow fiber membranes in a dried state are exposed to γ-ray (cf. Patent Literature 2). However, this method suffers from the following problems because of the protective agent contained in the hollow fiber membranes: that is, it is difficult to suppress the moisture content of the hollow fiber membranes lower; the protective agent tends to deteriorate due to the exposure to γ-ray; and it is needed to remove the protective agent by washing the hollow fiber membranes just before use.

There is disclosed a method of solving the above-discussed problems (cf. Patent Literature 3). According to this method, hollow fiber membranes of which the moisture content is not higher than 5% are exposed to a radioactive ray under an ambient atmosphere of not higher than 40% RH for their sterilization. This method is effective to solve the foregoing problems and to clear a criterion for the test regulated in the approval standards for manufacturing dialyzer type artificial kidney devices: that is, the UV absorbance (at a wavelength of 220 to 350 nm) of an extract from the hollow fiber membranes is lower than 0.1. However, this Patent Literature does not describe or suggest about the following problems: some influence of the ambient atmosphere (oxygen and water) around the hollow fiber membranes (or hollow fiber membrane modules) during the storage thereof acts to deteriorate (or oxidize and decompose) the materials of the hollow fiber membranes; and the UV absorbance of the extract (or the amount of an eluate) from the hollow fiber membranes tends to increase with time because of the deterioration of the materials of the hollow fiber membranes.

In the meantime, there is disclosed a method of suppressing the insoluble component of the materials of hollow fiber membranes to not higher than 10 wt. % by exposing the hollow fiber membranes to γ-ray with their moisture content maintained at not higher than 10 wt. % (cf. Patent Literature 4). It is described in this Patent Literature that the amount of a hydrophilic polymer which is extracted from membranes using a 40% aqueous ethanol solution is not larger than 2.0 mg/m$^2$ per one m$^2$ of the area of a surface of the membrane on its side in contact with a treated fluid.

The present inventors have intensively studied in order to improve the above-described sterilization methods by way of exposure to a radioactive ray or an electron ray. As a result, they have found that the sterilization method by way of exposure to a radioactive ray or an electron ray induces the formation of hydrogen peroxide which can not be detected by the above conventional UV absorption spectrometry. As a result of this finding, it is found that a hydrophilic polymer is extracted by the above extraction method. While the mechanism of forming hydrogen peroxide is unknown, the following can be supposed: the deterioration of the base materials of selectively permeable separation membranes is induced in the presence of hydrogen peroxide; hydrogen peroxide has an influence on the increase of the amount of an eluate from the membranes, which is detected by the above UV absorbance; and the amount of hydrogen peroxide itself tends to increase with time, which further accelerates the deterioration of the materials to thereby increase the amounts of the known extracts from the membranes. Accordingly, it is known that strict control is needed for the exposure of hollow fiber membranes to the radioactive ray or the electron ray and for the subsequent storage of the hollow fiber membranes in order to ensure safety as a blood purifier.

In the meantime, Patent Literature 3 and Patent Literature 4 do not refer to the formation of hydrogen peroxide during the storage of hollow fiber membranes and hollow fiber membrane modules, or to an absorbance (or an eluate) which tends to increase with time after the exposure to γ-ray, or to an increase in amount of a hydrophilic polymer (polyvinyl pyrrolidone) in an extract from the membranes using a 40% aqueous ethanol solution. Patent Literature 4 does not refer to the influence of a humidity of an ambient atmosphere around the hollow fiber membranes, which is given on the deterioration of the materials of the hollow fiber membranes.

To prevent the deterioration of the base materials of medical devices attributed to the presence of oxygen, it is known that the medical devices are sealed in packaging media made of oxygen impermeable materials, together with oxygen scavengers, and are then exposed to radioactive rays, and it is also disclosed that this method can be applied to blood purifiers (cf. Patent Literature 5, Patent Literature 6 and Patent Literature 7).

The deterioration of hollow fiber membranes because of the above radiation exposure in the presence of the oxygen scavenger is accompanied by odors (described in Patent Literature 5), a decrease in strength or dialyzing performance of the base materials (described in Patent Literature 6) or a decrease in strength of the base materials or formation of aldyhydes (described in Patent Literature 7). However, any of these Patent Literatures does not refer to an increase in amount of the above extract. Further, any of these Patent Literatures refers to the oxygen concentration in the package under the radiation exposure, but not to the importance of the moisture content of the selectively permeable separation membranes and the humidity of the ambient atmosphere.

Further, it is described that a material for the packaging bag for use in the method of sterilizing the blood purifier by way of radiation exposure in a system using the above oxygen scavenger is important to have a gas-, particularly oxygen-impermeability. However, the moisture permeability of such a material is not referred to.

Patent Literatures 8 and 9 disclose hollow fiber membrane modules which can show decreased amounts of hydrophilic polymers and which use no filling fluid, by displacing the internal atmospheres of the hollow fiber membrane modules with inert gases. However, the oxygen concentrations in the atmospheres for the sterilization of the hollow fiber membrane modules are high, and therefore, it is impossible to completely inhibit the deterioration and decomposition of the materials of the hollow fiber membranes under the radiation exposures. Consequently, the amounts of eluates from the hollow fiber membrane modules can not be reduced, and there arises a further problem that the biocompatibility of the membranes becomes poor since the materials of the membranes are crosslinked by the radiation exposures.

Patent Literature 10 discloses a technique of sealing a fluid separation membrane module in a packaging bag. According to this Patent Literature, the fluid separation membrane module and the packaging bag are filled with deairing water before the storage of the fluid separation membrane module packed in the packaging bag, and the packaging bag is made of a material capable of shutting out an air so as to seal the membrane module. This technique is intended to prevent the fluid separation membranes from partially drying due to the gasification of the air which is caused by a change in the temperature of the atmosphere during the storage of the fluid separation membranes. However, in this technique, no attention is paid to an increase in transport cost attributed to the increased weight of the package or to the proliferation of bacteria during the storage of the membranes.

Patent Literature 1: JP-B-55-23620
Patent Literature 2: JP-A-8-168524
Patent Literature 3: JP-A-2000-288085
Patent Literature 4: JP-A-2001-205057
Patent Literature 5: JP-A-62-74364
Patent Literature 6: JP-A-62-204754
Patent Literature 7: WO98/58842
Patent Literature 8: JP-A-2001-170167
Patent Literature 9: JP-A-2003-245526
Patent Literature 10: JP-A-2004-195380

DISCLOSURE OF THE INVENTION

Problems to be Solved by the Invention

Objects of the present invention are to provide a blood purifier package which shows less amounts of eluates from its blood purifier, particularly from the materials of selectively permeable separation membranes, the eluates being attributed to the deterioration of the same materials and increasing in amounts with time after the exposure to a radioactive ray and/or an electron ray, and which is therefore highly reliable in safety in use for hemocatharsis, and to provide a process for manufacturing the same.

Means for Solving the Problems

The present invention relates to a blood purifier package which is obtained by packing a blood purifier comprising selectively permeable separation membranes as a main component, and which is characterized in that the blood purifier is packed and sealed together with an oxygen scavenger in a packaging material capable of shutting out an external air and water vapor, under a condition of a relative humidity of above 40% RH at 25° C.

The present invention also relates to a process for manufacturing a blood purifier package obtainable by packing a blood purifier which comprises selectively permeable separation membranes as a main component, and this process includes a step of sterilizing the blood purifier which is sealed together with an oxygen scavenger in a packaging material under an internal atmosphere of a relative humidity of above 40% RH at 25° C. within the packaging material.

Effect of the Invention

The reliability of the blood purifier of the present invention in safety for use in hemocatharis is markedly improved, because it becomes possible to inhibit the formation of various extracts from the blood purifier which are attributed to the deterioration of the materials of the blood purifier, particularly the deterioration of selectively permeable separation membranes and which tend to increase in amounts with time after the sterilization of the blood purifier.

BEST MODES FOR CARRYING OUT THE INVENTION

Preferably, the selectively permeable separation membranes to be used in the present invention comprise a hydrophobic polymer containing a hydrophilic polymer. As raw materials for the hydrophobic polymer to be used in the present invention, there are preferably used cellulose-based polymers such as regenerated cellulose, cellulose acetate and cellulose triacetate, polysulfone-based polymers such as polysulfone and polyethersulfone, polyaclyronitrile, polymethyl methacrylate, ethylene-vinyl alcohol copolymers, etc. Among them, cellulose-based polymers and polysulfone-based polymers are preferable, because the use of them facilitates the manufacturing of selectively permeable separation membranes having a water permeability of 150 mL/m²/mmHg or more. Cellulose diacetate and cellulose triacetate are preferable among the cellulose-based polymers, because the use of them makes it easy to reduce the thickness of membranes. Polysulfone-based polymer represents a generic name of resins having sulfone bonds, and preferable examples thereof include, but not limited to, polysulfone resins and polyethersulfone resins having repeating units of the following formulas, which are commercially available with ease:

[Chemical formula 1]

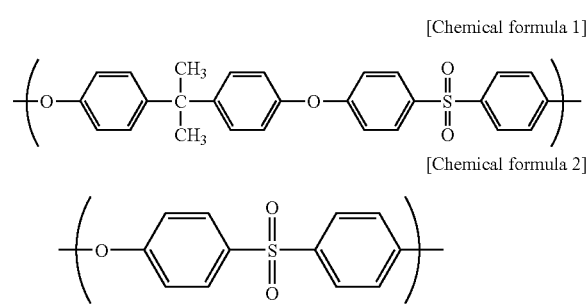

[Chemical formula 2]

Examples of the hydrophilic polymer to be used in the present invention include materials such as polyethylene glycol, polyvinyl alcohol, carboxylmethyl cellulose, polyvinyl pyrrolidone etc., which form micro phase separation structures with the hydrophobic polymers in solutions. In view of safety and cost, the use of polyvinyl pyrrolidone is preferred. It is preferable to use polyvinyl pyrrolidone having a higher molecular weight of, preferably from 10,000 (e.g. K-15 of BASF) to 1,200,000 (e.g. K-90 of BASF), more preferably from 100,000 to 1,200,000, still more preferably from 250,000 to 1,200,000, far still more preferably from 450,000 to 1,200,000, particularly from 600,000 to 1,200,000.

As the selectively permeable separation membranes of the present invention, either flat membranes or hollow fiber membranes may be used. However, hollow fiber membranes are preferable, because the membrane area per volume of a blood purifier can be increased, so that a compact blood purifier having a higher dialyzing efficiency can be obtained by using hollow fiber membranes.

The selectively permeable separation membranes and the blood purifier of the present invention can be manufactured by known processes. For example, the hollow fiber type selectively permeable separation membranes are manufactured by extruding a membrane-forming dope from the sheath portion of a double hollow spinneret and extruding an internal injection solution which is to keep the hollow portions of the membranes, from the core portion of the spinneret, followed by immersing the extruded semi-solid hollow fiber membranes in a solidifying fluid. Preferably, the hollow fiber membranes manufactured by this method should have inner diameters of 130 to 280 μm and thickness of 10 to 70 μm.

For example, the blood purifier of the present invention is manufactured by inserting a bundle of the above hollow fiber membranes into a housing for the blood purifier, pouring a potting agent such as polyurethane in both ends of the membrane bundle to thereby seal both ends thereof, cutting off an excess of the potting agent from both ends thereof to open the end faces of the hollow fiber membranes, and attaching a header to the housing.

In the present invention, the blood purifier obtained by the above method is packed and sealed together with an oxygen scavenger in a packaging material capable of shutting out an external air and water vapor under a condition of relative humidity of above 40% RH at 25° C. This is because a high relative humidity tends to inhibit increases in the amounts of eluates from the blood purifier, although the reason therefor is not well known. Therefore, the relative humidity is more preferably 45% RH or higher, still more preferably 50% RH or higher. When the relative humidity is not higher than 40% RH, the deteriorated substance determined by the measurement of UV absorbance, i.e. the hydrophilic polymer component is likely to increase with time after the sterilization of the blood purifier. In the meantime, particularly when the moisture content of the hydrophilic polymer is decreased, the wettability of the hollow fiber membranes tends to lower when such hollow fiber membranes are again wetted, or the hydrophilic polymer tends to elute from the hollow fiber membranes. Accordingly, the scope of the present invention also includes a means for compensating for an insufficient humidity of the internal atmosphere of the packaging bag by charging a humidity-controlled gas into the internal atmosphere of the packaging bag so that the humidity therein can satisfy the above specified range. A higher and higher relative humidity in the internal atmosphere of the packaging bag is preferred because the deterioration and decomposition of the hydrophilic polymer can be inhibited to thereby improve the storage stability of the blood purifier. However, too high a relative humidity is likely to permit dewing within the packaging bag and to degrade the quality of the blood purifier. Accordingly, the relative humidity is more preferably not higher than 95% RH, still more preferably not higher than 90% RH.

While it is unknown why the deterioration of the hydrophilic polymer (e.g. polyvinyl pyrrolidone) is inhibited by controlling the relative humidity of the inner atmosphere of the packaging bag to above 40% RH (at 25° C.), the following are supposed to inhibit such deterioration.

The deterioration of polyvinyl pyrrolidone is accelerated in the presence of oxygen. In the present invention, the inner atmosphere of the packaging bag is so maintained that the oxidation of polyvinyl pyrrolidone can be inhibited: in other words, the inner atmosphere of the packaging bag is maintained substantially in an anoxia state. However, it is difficult to perfectly control the oxygen concentration in the inner atmosphere of the packaging bag to zero, and a negligibly small amount of oxygen is present in the packaging bag. While no definite reason has been known, oxidation of polyvinyl pyrrolidone takes place when the negligibly small amount of oxygen in the packaging bag contacts polyvinyl pyrrolidone present in the surfaces of the hollow fiber membranes. This oxidation is supposed to form radicals in a system free of water, and the formed radicals are supposed to attack and deteriorate polyvinyl pyrrolidone. The deterioration of polyvinyl pyrrolidone further facilitates the formation of radicals, with the result that the deterioration of polyvinyl pyrrolidone acceleratedly proceeds and gradually spreads in a whole of the hollow fiber membranes. On the other hand, in a system containing water therein, oxidation between oxygen and polyvinyl pyrrolidone takes place without forming any radical. It is supposed that further deterioration of polyvinyl pyrrolidone does not proceed after the oxygen in the system (i.e. the packaging bag) has been consumed. Since polyvinyl pyrrolidone is a highly water-absorbable material, it is sufficient for the system (i.e. the packaging bag) to contain a minimum critical amount of water for wetting polyvinyl pyrrolidone. In the present invention, the moisture content of the hollow fiber membranes is sufficient to be 2.5 mass % or so. However, it is needed to control the relative humidity in the packaging bag to above 40% RH in order to prevent the evaporation of water in the hollow fiber membranes, since too low a relative humidity in the packaging bag permits the evaporation of water in the hollow fiber membranes with time.

In the present invention, preferably, the blood purifier is sealed together with an oxygen scavenger in a packaging bag and is then exposed to a radioactive ray and/or an electron ray for the sterilization thereof. Examples of the radioactive ray or the electron ray to be used in the present invention are α-ray, β-ray, γ-ray, electron ray, etc. In view of sterilization efficiency and handling ease, γ-ray or an electron ray is preferably employed. While not limited, the dose of a radioactive ray or an electron ray is such that the sterilization of the blood purifier can be ensured. In general, the dose thereof is preferably from 10 to 50 kGy. When the dose of a radioactive ray or an electron ray is too small, the blood purifier is unlikely to be perfectly sterilized. On the contrary, when it is too large, such an intensified dose is likely to deteriorate and decompose the materials of the membranes and the housing and the adhesive resin. Accordingly, the dose of a radioactive ray or an electron ray is more preferably from 10 to 30 kGy.

The above-described effect also can be exhibited when the preceding condition is maintained not only after the sterilization treatment but also before the same. When this condition is maintained during the sterilization treatment, increases in the amounts of the above extracts attributed to the exposure to a radioactive ray or an electron ray can be inhibited. Accordingly, it is preferable to maintain the above specified condition at least when the sterilization treatment is carried out.

In the present invention, the moisture content of the selectively permeable separation membrane is preferably 2.5 mass % or lower, more preferably 2.3 mass % or lower, still more preferably 2.0 mass % or lower, far still more preferably 1.8 mass % or lower. When the moisture content of the selectively permeable separation membrane exceeds 2.5 mass %, there are likely to arise similar problems to those which occur in the conventional sterilization method under wet conditions: that is, the weight of the blood purifier increases, and bacteria are apt to proliferate. There are also likely to arise some problems when the bundle of such hollow fiber membranes is fixed to the housing with an urethane adhesive etc.: that is, there is a failure in adhesion of the bundle of the hollow fiber membranes because of the foaming of the resin; or an eluate from the membranes tends to increase in amount because of the reaction of the adhesive with water. For these reasons, the lower the moisture content of the selectively permeable separation membranes, the better. However, too low a moisture content of the membranes is, on the contrary, likely to increase the amount of the eluate from the blood purifier, although why such an event occurs is not well known. Accordingly, the moisture content of the membranes is preferably not lower than 1.0 mass %, more preferably not lower than 1.2 mass %.

In the present invention, a method for adjusting the moisture content of the selectively permeable separation membrane within the above specified range may be optionally selected. A blood purifier comprising selectively permeable separation membranes with the above moisture content as a main component which are assembled into a module may be packed and sealed in a packaging bag. Otherwise, a blood purifier comprising selectively permeable separation membranes which are dried to a moisture content of 0.5 mass % or lower and which are assembled into a module may be adjusted in moisture to thereby control the moisture content of the membranes. In the latter moisture adjustment, the blood purifier may be sealed in a packaging bag after the moisture content of the membranes has been adjusted, or may be adjusted in moisture within the packaging bag so as to adjust the moisture content of the membranes.

In the present invention, the relative humidity is calculated from a partial vapor pressure (p) and a saturated vapor pressure (P) at room temperatures, by the equation: Relative Humidity (%)=p/P×100. This measurement is conducted as follows: the sensor probe of a temperature- and humidity-measuring instrument (ONDOTORI RH Type manufactured by T&D) is inserted into a packaging bag, and then, the bag is sealed to continuously measure the relative humidity within the bag.

In the present invention, the moisture content (mass %) of the hollow fiber membrane can be easily calculated by the following equation:

Moisture content (mass %)=$(a-b)/a \times 100$ wherein (a) represents the mass of the hollow fiber membrane before drying, and (b) represents the mass of the bone-dried hollow fiber membrane after drying in an oven at 120° C. for 2 hours. Herein, by adjusting the mass (a) of the hollow fiber membrane to from 1 to 2 g, the hollow fiber membrane can be bone-dried (i.e. a dried state in which the hollow fiber membrane shows no further change in mass) in 2 hours.

In the present invention, a method for adjusting the relative humidity to above 40% RH at 25° C. in the internal atmosphere of the packaging bag may be optionally selected. For example, the relative humidity may be adjusted by the moisture content of the selectively permeable separation membranes; or a gas adjusted in humidity may be charged into the packaging bag. While the gas to be used is not limited, the use of an inert gas (e.g. nitrogen, argon, etc.) is preferable since the use of such an inert gas is effective to inhibit the oxidation and deterioration of the blood purifier as will be described later.

The oxygen scavenger to be used in the present invention is not limited, in so far as it has a deoxygenating action. Examples of the oxygen scavenger of the present invention are oxygen scavengers which contain, as main oxygen-absorbing agents, sulfite, hydrogensulfite, dithionite, hydroquinone, catechol, resorcinol, pyrogallol, gallic acid, rongalite, ascorbic acid and/or a salt thereof, sorbose, glucose, lignin, dibutylhydroxytoluene, dibutylhydroxyanisole, ferrous salt, metal powder (e.g. iron powder, etc.) etc. The oxygen scavenger may be appropriately selected from these materials for use. To an oxygen scavenger which mainly comprises metal powder, if needed, an oxidation catalyst may be added. As the oxidation catalyst, there can be used one or more compounds selected from halogenated metal compounds such as sodium chloride, potassium chloride, magnesium chloride, calcium chloride, aluminum chloride, ferrous chloride, ferric chloride, sodium bromide, potassium bromide, magnesium bromide, calcium bromide, iron bromide, nickel bromide, sodium iodide, potassium iodide, magnesium iodide, calcium iodide, iron iodide, etc. The oxygen scavenger may optionally contain a deodorant or other functional filler. The form of the oxygen scavenger is not limited, and it may be in the form of powder, particles, mass or sheet; or it may be a sheet- or film-shaped oxygen scavenger obtained by dispersing an oxygen absorber composition in a thermoplastic resin.

Preferably, the packaging bag to be used in the present invention is made of an oxygen- or water vapor-impermeable material. This is because the use of such a material is effective to maintain the humidity and the oxygen concentration of the sealed atmosphere within the above-specified ranges over a long period of time, to thereby inhibit the aged deterioration of the materials of the blood purifier before and after the exposure, and to thereby inhibit an increase in the amount of the extract from the blood purifier. Accordingly, the oxygen permeability of the material for the packaging bag is preferably at most 1 cm³/(m².24 hr.atm) (20° C., 90% RH), and the water vapor permeability thereof is preferably at most 5 g/(m².24 hr.atm) (40° C., 90% RH).

The oxygen permeability of the material for the packaging bag is more preferably at most 0.9 cm³/(m².24 hr.atm) (20° C., 90% RH), still more preferably at most 0.8 cm³/(m².24 hr.atm) (20° C., 90% RH), particularly at most 0.7 cm³/(m².24 hr.atm) (20° C., 90% RH) . The water vapor permeability thereof is more preferably at most 4 g/(m².24 hr.atm) (40° C., 90% RH), still more preferably at most 3 g/(m².24 hr.atm) (40° C., 90% RH), particularly at most 2 g/(m².24 hr.atm) (40° C., 90% RH).

The material and structure of the packaging bag to be used in the present invention may be optionally selected, so long as the above characteristics are satisfied. Preferable examples of the material for the packaging bag are oxygen- and water vapor-impermeable materials such as an aluminum foil, aluminum-deposited film, inorganic oxide-deposited film of silica and/or alumina, vinylidene chloride polymer composite film, etc. The sealing method for the packaging bag also may be optionally selected. For example, the packaging bag may be sealed by any of the heat sealing method, impulse heat sealing method, fusion sealing method, frame sealing method, ultrasonic sealing method, high frequency sealing method, etc. Thus, preferable as the material for the packaging bag is a composite material of a film having a sealing property and any of the above impermeable materials. Particularly preferable is a laminate sheet having both of impermeability and a heat sealing property, which comprises a structural layer of an aluminum foil capable of substantially shutting out an oxygen gas and a water vapor, an outer layer of a polyester film, an intermediate layer of an aluminum foil, and an inner layer of a polyethylene film.

In the present invention, the oxygen present within the packaging bag is absorbed by the oxygen scavenger to thereby lower the oxygen concentration of the internal atmosphere of the packaging bag, so that there can be inhibited the aged oxidation and deterioration of the selectively permeable separation membranes, the adhesive and the materials of the housing, etc. which constitute the blood purifier, during, before and after the exposure of the blood purifier to a radioactive ray or an electron ray. Thus, the foregoing extracts from the blood purifier, which increase in amounts during the exposure or with time, can be inhibited. Accordingly, it is preferable to expose the blood purifier to a radioactive ray or an electron ray, on the condition that the oxygen concentration within the packaging bag has been sufficiently decreased. The oxygen concentration within the packaging bag during the exposure to a radioactive ray or an electron ray is preferably not higher than 5%, more preferably not higher than 3%, still more preferably not higher than 1%, far still more preferably not higher than 0.5%, particularly lower than 0.1%. For example, when the gas in the inner atmosphere of the bag is an air, the oxygen concentration of the inner atmosphere of the bag usually decreases to 0.1% or lower after 48 hours or so has passed since the blood purifier was sealed in the packaging bag, although this time differs depending on the type or performance of the oxygen scavenger used. Accordingly, preferably, it is at least 2 days after the sealing of the bag that the blood purifier in the packaging bag should be exposed to a radioactive ray or an electron ray. In this regard, too long a time interval between the sealing of the bag and the sterilization of the blood purifier is likely to permit the proliferation of bacteria, and thus, the sterilization of the blood purifier should be done preferably within 10 days, more preferably within 7 days, still preferably 5 days, after the sealing of the bag.

Preferably, the blood purifier of the present invention should satisfy the following amounts of extracts therefrom when used for hemodialysis.

(1) The UV absorbance of an extract at 220 to 350 nm according to the approved standards for manufacturing dialyzer type artificial kidney devices is lower than 0.10.

(2) The amount of a hydrophilic polymer extracted from the blood purifier, using a 40% aqueous ethanol solution is not larger than 2.0 mg/m² per 1.0 m² of a surface of the membrane on the treated fluid-contacting side.

In the known technologies, keen attentions have been paid to the amounts of the extracts (1) and (2) as the values found just after the sterilizing treatment. However, these known technologies pay quite no attention to the amounts of the above extracts which tend to increase with time after the sterilizing treatment. It can be said that, by the present invention accomplished by paying keen attentions to these novel events and elucidating these events, the reliability of the blood purifier in safety can be markedly improved.

Hereinafter, the main and preferred embodiments of the present invention will be described below.

[1] A blood purifier package obtained by packing a blood purifier comprising selectively permeable separation membranes as a main component, characterized in that the blood purifier is packed and sealed together with an oxygen scavenger in a packaging material capable of shutting out an external air and a water vapor, under a condition of a relative humidity of above 40% RH at 25° C.

[2] A blood purifier package which is defined in the above item [1] and which is characterized in that the moisture content of the selectively permeable separation membrane is not larger than 2.5 mass %.

[3] A blood purifier package which is defined in the above item [1] or [2] and which is characterized in that the selectively permeable separation membrane comprises a hydrophobic polymer containing a hydrophilic polymer.

[4] A blood purifier package which is defined in the above item [3] and which is characterized in that the hydrophobic polymer is a polysulfone-based polymer.

[5] A blood purifier package which is defined in the above item [3] or [4] and which is characterized in that the hydrophilic polymer is polyvinyl pyrrolidone.

[6] A blood purifier package which is defined in any of the above items [1] to [5] and which is characterized in that the oxygen permeability of the packaging material is not larger than 1 cm³/(m².24 hr.atm) (20° C. and 90% RH).

[7] A blood purifier package which is defined in any of the above items [1] to [6] and which is characterized in that the water vapor permeability of the packaging material is not larger than 5 g/(m².24 hr.atm) (40° C. and 90% RH).

[8] A process for manufacturing a blood purifier package obtainable by packing a blood purifier which comprises selectively permeable separation membranes as a main component, characterized in that the process includes a step of sterilizing the blood purifier which is packed and sealed together with an oxygen scavenger in a packaging material, under an atmosphere of a relative humidity of above 40% RH at 25° C.

[9] A process which is defined in the above item [8] and which is characterized in that the moisture content of the selectively permeable separation membrane is not larger than 2.5 mass %.

[10] A process which is defined in the above item [8] or [9] and which is characterized in that the selectively permeable separation membrane comprises a hydrophobic polymer containing a hydrophilic polymer.

[11] A process which is defined in the above item [10] and which is characterized in that the hydrophobic polymer is a polysulfone-based polymer.

[12] A process which is defined in the above item [10] or [11] and which is characterized in that the hydrophilic polymer is polyvinyl pyrrolidone.

[13] A process which is defined in any of the above items [8] to [12] and which is characterized in that the oxygen permeability of the packaging material is not larger than 1 $cm^3/(m^2 \cdot 24\ hr.atm)$ (20° C. and 90% RH).

[14] A process which is defined in any of the above items [8] to [13] and which is characterized in that the water vapor permeability of the packaging material is not larger than 5 $g/(m^2 \cdot 24\ hr.atm)$ (40° C. and 90% RH).

EXAMPLES

Hereinafter, the effects of the present invention will be described by Examples thereof, which, however, should not be construed as limiting the scope of the present invention in any way. The physical properties of the following Examples were evaluated as follows.

1. Calculation of the Area of Membranes

The area of membranes in a dialyzer was calculated by the following equation, based on the inner diameter of the hollow fiber membrane:

$$A(m^2) = n \times \pi \times d \times L$$

[in the equation, n represents the number of hollow fiber membranes in the dialyzer; π represents the ratio of the circumference of a circle to its diameter; d represents the inner diameter (m) of the hollow fiber membrane; and L represents the effective length (m) of the hollow fiber membranes in the dialyzer].

2. UV Absorbance (at 220 to 350 nm) According to Approved Standards for Manufacturing Dialyzer Type Artificial Kidney Devices Extraction and measurement were conducted according to the method regulated in the approved standards for manufacturing dialyzer type artificial kidney devices. A sample of hollow fiber membranes (1 g) was admixed with pure water (100 mg), and the mixture was subjected to extraction at 70° C. for one hour to prepare a test solution. Then, the UV absorbance of this test solution at a wavelength of 220 to 350 nm was measured. According to the above standard, the maximum absorbance is regulated to be lower than 0.1.

3. Amount of Hydrophilic Polymer Extracted with 40% Aqueous Ethanol Solution

A case of polyvinyl pyrrolidone (PVP) as an example of hydrophilic polymers is described.

A module with its passage on the dialysing fluid side closed was connected to a silicone tube circuit, and pure water was allowed to pass through the passage on the blood side of the module to fill both the module and the circuit with pure water. After that, a 40 v/v % ethanol solution was allowed to pass through the passage on the blood side of the module at a flow rate of 150 ml/min., and 100 ml of the same solution was discharged from the outlet of the circuit. The inlet and the outlet of the passage on the blood side were closed with forceps, and the passage on the dialyzing fluid side was successively filled with the 40 v/v % ethanol solution, and was again closed. The 40 v/v % ethanol solution, the circuit and the module were all controlled to 40° C., and the ethanol solution was circulated at a flow rate of 150 ml/min. Sixty minutes after, all the fluids in the circuit and the module were discharged and collected together with the circulating fluid to measure the volume of the mixture. The fluid on the dialysing fluid side was separately collected to measure its volume. The PVP contents of the respective fluids were measured according to the following procedure. A sample of each fluid (2.5 ml) was admixed with 0.2 mol/L citric acid (1.25 ml), and the mixture was stirred. Then, 0.006N iodine (500 µL) was added, and the resulting mixture was stirred and was left to stand at a room temperature for 10 minutes. After that, the absorbance of the resultant solution at 470 nm was measured. When the PVP content of the solution was high, the solution was diluted to be 10 or 100 times larger in volume, and then, the PVP content was measured. The PVP content in the sample was calculated from an analytical curve prepared under the same conditions, to thereby calculate the amount of eluted PVP ($mg/m^2$) per module (1.0 $m^2$).

4. Oxygen Concentration in Packaging Bag

The measurement was conducted by gas chromatography, using a column filled with a molecular sieve (13X-S mesh 60/80 manufactured by GL Science), an argon gas as a carrier gas, and a detector of heat-conduction system. An analysis was made at a column temperature of 60° C. A gas within a packaging bag was collected by directly pricking the closed packaging bag with a syringe needle.

5. Oxygen Permeability of Packaging Material

An oxygen permeability-measuring apparatus (OX-TORAN 100 manufactured by Modern Controls) was used to measure the oxygen permeability of the material of the packaging bag at 20° C. and 90% RH.

6. Water Vapor Permeability of Packaging Material

A water vapor permeability-measuring apparatus (PARMATRAN-W manufactured by Modern Controls) was used to measure the waver vapor permeability of the material of the packaging bag at 40° C. and 90% RH.

7. Moisture Content of Hollow Fiber Membrane

To find a moisture content (mass %) of a hollow fiber membrane, the mass (a) of the hollow fiber membrane before dried and the mass (b) of the same hollow fiber membrane after dried at 120° C. in an oven for 2 hours (bone-dried) were measured. The moisture content was calculated by the following equation:

Moisture content (mass %) = $(a-b)/a \times 100$ wherein, if (a) is from 1 to 2 g, the hollow fiber membrane could be bone-dried in 2 hours (if bone-dried, the membrane shows no further change in mass).

Example 1

A spinning dope was prepared from polyethersulfone (5200P, manufactured by Sumika Chemtex Company, Limited) (18.0 mass %), polyvinyl pyrrolidone (K90 manufactured by BASF) (4.2 mass %) as a hydrophilicity-imparting agent, water (1.8 mass %) as a non-solvent, triethylene glycol (TEG manufactured by MITSUI CHEMICALS, INC.) (30.4 mass %) and dimethylacetamide (DMAc manufactured by Mitsubishi Gas Chemical Company, Inc.) (45.6 mass %). The spinning dope was extruded from the outer slit of a double spinneret maintained at 45° C., and water as an inner solution was extruded from the inner injection hole of the double spinneret. The extruded semi-solid hollow fiber was allowed to pass through an air gap with a length of 600 mm at a spinning rate of 60 m/minute, and was then dipped in a solidifying bath of 70° C. (DMAc:TEG:water=12:8:80). After that, the hollow fiber was washed with RO water of 45° C. for 60 seconds followed by RO water of 80° C. for 90 seconds, and then was wound onto a hank. Thus, the hollow fiber membrane with an inner diameter of 200.3 µm and a thickness of 28.0 µm was obtained.

A bundle of about 10,000 hollow fiber membranes thus obtained was inserted into a polyethylene pipe, which was then cut with a predetermined length. After that, the hollow fiber membranes in the pipe were wetted. The resulting wet bundle was dried in a hot air drier of 40° C. until the moisture content of the selectively permeable separation membranes became 2.1 mass %. Thus, the dry bundle of the membranes was obtained.

The bundle was inserted into a housing casing, and the end portions of the bundle were bonded and fixed with an urethane resin. Then, the end portions of the bundle were cut out to thereby obtain a blood purifier which comprised the selectively permeable separation membranes opened at both ends thereof. This blood purifier was packed and sealed together with two general-purpose oxygen scavengers (TAMOTSU manufactured by OJITACK Co., Ltd.) in a packaging bag made of an aluminum laminate sheet. In this regard, the aluminum laminate sheet had an outer layer of a polyester film, an intermediate layer of an aluminum foil and an inner layer of a polyethylene film, and had an oxygen permeability of 0.5 cm$^3$/(m$^2$.24 hr.atm) and a water vapor permeability of 0.5 g/(m$^2$.24 hr.atm). The packaging bag was sealed after the inner atmosphere of the packaging bag was displaced with an air adjusted in humidity to 70% RH. After the sealing, the packaging bag was stored at room temperature for 48 hours to thereby scavenge the oxygen within the system, and was then exposed to γ-ray at a dose of 20 kGy for the sterilization of the blood purifier in the packaging bag. After the sterilization, the packaging bag was stored in a storehouse under an atmosphere of room temperature (25° C.) and 30% RH. One day, one month and three months after the storage of the packaging bag, the humidity and oxygen concentration of the internal atmosphere of the packaging bag, the moisture content of the selectively permeable separation membrane, the UV absorbance of an eluate from the blood purifier in an elution test and the amount of extracts from the blood purifier were measured, respectively. The results are shown in Tables 1 to 3.

Comparative Example 1

Hollow fiber membranes and a dry bundle of the same hollow fiber membranes were obtained in the same manners as in Example 1.

A blood purifier was assembled in the same manner as in Example 1, using the resultant dry bundle of the hollow fiber membranes. A blood purifier package was obtained in the same manner as in Example 1, except that the humidity-controlling was not done when the blood purifier was sealed in a packaging bag, and the resultant purifier package was stored under the same conditions as in Example 1. The results of the evaluation of the selectively permeable separation membranes, which had changed with time, are shown in Tables 1 to 3. The amounts of eluates from the blood purifier increased. It was supposed that the drying of the hollow fiber membranes proceeded during the storage thereof since no humidity-controlling was done, and therefore that the intertwining of the hydrophilic polymer and the hydrophobic polymer became weak to allow the eluates from the blood purifier.

Comparative Example 2

In the process of Example 1, the drying of a wet bundle of the selectively permeable separation membranes was intensified to obtain the bundle of the membranes of which the moisture content was decreased to 0.6 mass % immediately after completion of the drying.

A blood purifier was assembled using the resultant selectively permeable separation membranes in the same manner as in Example 1. A blood purifier package was obtained in the same manner as in Example 1, except that the blood purifier was sealed in a packaging bag without any oxygen scavenger, and the resultant blood purifier package was stored under the same conditions as in Example 1. The results of the evaluation of the blood purifier, which had changed with time, are shown in Tables 1 and 2. The eluates from the blood purifier increased in amount with time, because the oxidation and decomposition of the hydrophilic polymer proceeded due to the influence of oxygen in the system and due to the synergic effect of the oxygen and the γ-ray exposure.

Comparative Example 3

A blood purifier package was obtained in the same manners as in Example 1, except that no humidity-controlling was done and that no oxygen scavenger was used. The resultant blood purifier package was stored under the same conditions as in Example 1. The results of the evaluation of the blood purifier, which had changed with time, are shown in Tables 1 to 3. Like Comparative Example 2, the eluates from the blood purifier increased in amount with time, because the oxidation and decomposition of the hydrophilic polymer proceeded due to the influence of oxygen in the system.

Example 2

A blood purifier package was obtained in the same manners as in Example 1, except that an electron-exposure machine whose acceleration voltage was 5,000 KV was used instead of the exposure to γ-ray. The results of the evaluation of the blood purifier, which had changed with time, are shown in Tables 1 to 3.

Comparative Example 4

A blood purifier package was obtained in the same manners as in Example 1, except that the blood purifier was sealed in a packaging bag having an oxygen permeability and a vapor permeability. The resultant blood purifier package was stored under the same conditions as in Example 1. The results of the evaluation of the blood purifier, which had changed with time, are shown in Tables 1 to 3. An oxygen in an external atmosphere infiltrated the packaging bag because of the high oxygen permeability of the packaging bag, and the drying of the hollow fiber membranes proceeded because of the high vapor permeability of the packaging bag. As a result, the oxidation and decomposition of the hydrophilic polymer proceeded, and the eluates from the blood purifier increased in amount with time.

TABLE 1

|  | Moisture content (mass %) | Relative humidity in bag (% RH) | Oxygen scavenger | Oxygen permeability of bag (cm$^2$/(m$^2$·24 h·atm)) | Water vapor permeability of bag (g/(m$^2$·24 h·atm)) |
| --- | --- | --- | --- | --- | --- |
| Ex. 1 | 2.1 | 70 | Present | 0.5 | 0.5 |
| Ex. 2 | 2.1 | 70 | Present | 0.5 | 0.5 |
| C. Ex. 1 | 2.1 | 30 | Present | 0.5 | 0.5 |
| C. Ex. 2 | 0.6 | 70 | Absent | 0.5 | 0.5 |
| C. Ex. 3 | 2.1 | 30 | Absent | 0.5 | 0.5 |
| C. Ex. 4 | 2.1 | 70 | Present | 600 | 10 |

TABLE 2

| | Just after sterilization | | | 1 month after sterilization | | | 3 months after sterilization | | |
| --- | --- | --- | --- | --- | --- | --- | --- | --- | --- |
| | Moisture content (mass %) | Relative humidity (% RH) | Oxygen concentration (%) | Moisture content (mass %) | Relative humidity (% RH) | Oxygen concentration (%) | Moisture content (mass %) | Relative humidity (% RH) | Oxygen concentration (%) |
| Ex. 1 | 2.1 | 70 | ND | 2.0 | 68 | ND | 2.1 | 72 | ND |
| Ex. 2 | 1.8 | 69 | ND | 2.0 | 70 | ND | 1.9 | 68 | ND |
| C. Ex. 1 | 2.1 | 35 | ND | 1.7 | 36 | ND | 1.1 | 35 | ND |
| C. Ex. 2 | 0.6 | 71 | 20 | 0.7 | 70 | 21 | 0.7 | 69 | 21 |
| C. Ex. 3 | 2.1 | 37 | 21 | 2.1 | 37 | 21 | 2.1 | 24 | 20 |
| C. Ex. 4 | 2.3 | 70 | 21 | 1.1 | 31 | 21 | 0.8 | 30 | 21 |

TABLE 3

| | Just after sterilization | | 1 month after sterilization | | 3 months after sterilization | |
| --- | --- | --- | --- | --- | --- | --- |
| | UV absorbance | Extract from ethanol (mg/m$^2$) | UV absorbance | Extract from ethanol (mg/m$^2$) | UV absorbance | Extract from ethanol (mg/m$^2$) |
| Ex. 1 | 0.03 | 1.3 | 0.04 | 1.3 | 0.04 | 1.4 |
| Ex. 2 | 0.05 | 1.4 | 0.04 | 1.4 | 0.04 | 1.4 |
| C. Ex. 1 | 0.07 | 1.8 | 0.15 | 2.5 | 0.15 | 2.8 |
| C. Ex. 2 | 0.05 | 1.5 | 0.16 | 2.8 | 0.27 | 3.3 |
| C. Ex. 3 | 0.04 | 1.3 | 0.22 | 3.0 | 0.36 | 4.2 |
| C. Ex. 4 | 0.04 | 1.3 | 0.09 | 2.1 | 0.33 | 4.1 |

INDUSTRIAL APPLICABILITY

There can be inhibited formation of various extracts from the blood purifiers of the present invention, which is attributed to the deterioration of the materials, particularly the selectively permeable separation membranes of the blood purifiers and which proceeds with time after the sterilization of the blood purifiers. Therefore, the reliability of such blood purifiers in safety in use for hemocatharsis is remarkably improved, and thus, the present invention will significantly contribute to this industry.

The invention claimed is:
1. A blood purifier package comprising
(a) a blood purifier comprising selectively permeable separation membranes as a main component, wherein the moisture content of the selectively permeable separation membranes is not lower than 1.0 mass % and not larger than 2.1 mass %,
wherein the selectively permeable separation membranes comprise a polysulfone-based polymer containing polyvinyl pyrrolidone,
(b) an oxygen scavenger, and
(c) a packaging material capable of shutting out external air and water vapor, which packaging material is sealed and defines a space containing an atmosphere,
wherein
the oxygen permeability of the packaging material is not larger than 1 cm$^3$/(m$^2$.24 hr.atm) (20° C and 90% RH),
the water vapor permeability of the packaging material is not larger than 5 g/(m$^2$.24 hr.atm) (40° C and 90% RH),
the blood purifier and the oxygen scavenger are within the space defined by the sealed packaging material,
the atmosphere in the space has a relative humidity of not less than 68% RH at 25° C, and
the blood purifier has been sterilized by exposure of the blood purifier within the sealed packaging material to a radioactive ray, an electron ray, or both a radioactive ray and an electron ray, wherein the oxygen concentration within the sealed packaging material during sterilization is not higher than 5%.

* * * * *

UNITED STATES PATENT AND TRADEMARK OFFICE
CERTIFICATE OF CORRECTION

| | | |
|---|---|---|
| PATENT NO. | : 9,067,178 B2 | Page 1 of 1 |
| APPLICATION NO. | : 11/721766 | |
| DATED | : June 30, 2015 | |
| INVENTOR(S) | : Mabuchi et al. | |

It is certified that error appears in the above-identified patent and that said Letters Patent is hereby corrected as shown below:

On the title page:

(22) PCT Filed

"Dec. 2, 2005" should read "Dec. 20, 2005"

(30) Foreign Application Priority Data

"Dec. 22, 2004   (JP)   P2004-371542" should read "Dec. 22, 2004   (JP)   2004-371542"

Signed and Sealed this
Twenty-second Day of December, 2015

Michelle K. Lee
*Director of the United States Patent and Trademark Office*